US007982877B2

(12) United States Patent
Maveyraud et al.

(10) Patent No.: US 7,982,877 B2
(45) Date of Patent: Jul. 19, 2011

(54) METHOD FOR MEASURING THE ANISOTROPY IN AN ELEMENT COMPRISING AT LEAST ONE FISSILE MATERIAL AND A CORRESPONDING INSTALLATION

(75) Inventors: Grégory Maveyraud, Mornac (FR); Jean-Marie Vallerot, Brive la Gaillarde (FR); Xavier Bourrat, Bordeaux (FR); Olivier Dugne, Orange (FR)

(73) Assignees: Areva NP, Courbevoie (FR); Commissariat a l'Energie Atomique et aux Energies Alternatives, Paris (FR)

( * ) Notice: Subject to any disclaimer, the term of this patent is extended or adjusted under 35 U.S.C. 154(b) by 582 days.

(21) Appl. No.: 11/914,999

(22) PCT Filed: May 16, 2006

(86) PCT No.: PCT/IB2006/001289
§ 371 (c)(1),
(2), (4) Date: Mar. 31, 2008

(87) PCT Pub. No.: WO2006/126051
PCT Pub. Date: Nov. 30, 2006

(65) Prior Publication Data
US 2008/0231855 A1    Sep. 25, 2008

Related U.S. Application Data

(60) Provisional application No. 60/687,068, filed on Jun. 3, 2005.

(30) Foreign Application Priority Data

May 25, 2005 (FR) ...................................... 05 05276

(51) Int. Cl.
*G01J 4/00* (2006.01)
*G01B 11/30* (2006.01)
*G06K 9/00* (2006.01)
(52) U.S. Cl. ........................ 356/369; 356/600; 382/108
(58) Field of Classification Search ....................... None
See application file for complete search history.

(56) References Cited

U.S. PATENT DOCUMENTS

| 3,972,619 | A | 8/1976 | Stevens et al. | |
| 4,617,682 | A * | 10/1986 | Mori et al. | 382/108 |
| 5,028,138 | A | 7/1991 | Wolff et al. | |
| 7,127,280 | B2 | 10/2006 | Dauga | |
| 2001/0024277 | A1 | 9/2001 | Hirosawa et al. | |
| 2002/0093655 | A1* | 7/2002 | Everett et al. | 356/369 |
| 2003/0180966 | A1 | 9/2003 | Abbott et al. | |
| 2008/0170227 | A1* | 7/2008 | Schimming et al. | 356/364 |

FOREIGN PATENT DOCUMENTS

| EP | 0720036 A | 7/1996 |
| EP | 1128160 A | 8/2001 |
| FR | 2810737 | 12/2001 |

* cited by examiner

*Primary Examiner* — Tarifur Chowdhury
*Assistant Examiner* — Gordon J Stock, Jr.
(74) *Attorney, Agent, or Firm* — Connolly Bove Lodge & Hutz LLP

(57) ABSTRACT

This method comprises the steps of: transmitting a beam of light onto a surface (17) of an element (1) comprising a fissile material, passing the beam of light reflected by the surface into a polarisation analyser (27) having a modifiable analysis direction, transmitting the beam from the polarisation analyser (27) to a device (31) for acquiring digital images, acquiring at least one digital image (31) of the surface (17) of the element (1) and processing the digital image acquired in order to measure the anisotropy. Use, for example, in controlling particles of nuclear fuel for an HTR/VHTR type reactor.

14 Claims, 6 Drawing Sheets

METHOD FOR MEASURING THE ANISOTROPY IN AN ELEMENT COMPRISING AT LEAST ONE FISSILE MATERIAL AND A CORRESPONDING INSTALLATION

CROSS REFERENCE TO RELATED APPLICATIONS

This application is a National Phase filing under 35 U.S.C. §371 of PCT/IB2006/001289 filed May 16, 2006, which claims priority to Patent Application No. 0505276, filed in France on May 25, 2005 and Patent Application No. 60/687,068, filed in the United States on Jun. 3, 2005. The entire contents of each of the above-applications are incorporated herein by reference.

BACKGROUND OF THE INVENTION

The present invention relates to a method for measuring the anisotropy of a zone of the surface of an element comprising at least one fissile material, the method being of the type comprising the steps of:
transmitting a beam of light onto the surface and
passing the beam of light reflected by the surface into a polarisation analyser having a modifiable analysis direction.

The invention is used in particular, but not exclusively, for controlling particles of nuclear fuel for a high temperature nuclear reactor (HTR) or a very high temperature nuclear reactor (VHTR).

Such particles are generally spherical and comprise a fissile core which is surrounded by layers of dense and porous pyrocarbon and silicon carbide.

Those particles are intended to be embedded in graphite matrices in order to be able to be introduced into a reactor. Those matrices are, for example, in the form of ovoids or cylinders, sometimes referred to as compacts.

The quality of the layers of dense pyrocarbon determines the life-span of the particles during their irradiation in the reactor. Under irradiation, pyrocarbon tends to become anisotropic, which brings about a stressed state which may compromise the integrity and uniformity of the particles owing to rupture of the layer of silicon carbide.

At the end of the operation for producing the particles, therefore, their pyrocarbon layers must be as isotropic as possible and it is desirable to be able to control the degree of anisotropy thereof with tools suitable for rapid control of an industrial type.

U.S. Pat. No. 3,972,619 describes a method which allows the anisotropy of the pyrocarbon layers of such particles to be measured. The measurement is carried out on a metallographic section in an equatorial plane of a particle.

A beam of monochromatic polarised light is transmitted onto the sectioned surface of the particle. If the zone of that surface that is illuminated by that beam is not isotropic, it will bring about slight depolarisation of the beam when it is reflected. Rotation of the direction of the polarisation of the incident beam is brought about so that the polarisation direction of the reflected beam oscillates.

The amplitude of the oscillations is established by measuring the amplitude of the oscillations of the intensity detected by a photometer, after the reflected beam has been passed into a polarisation analyser. The analysis direction of the polarisation analyser is modified and measurements of the amplitude of the oscillations are carried out with different analysis directions.

Based on those different measurements, parameters characterising the anisotropy in the zone illuminated by the incident beam are calculated.

Such a method requires a relatively complex and costly installation, in particular because of the presence of the large number of pieces of optical equipment and the photometer. The method is also found to take a long time to carry out.

There have also been envisaged methods for measuring the anisotropy which were not optical methods, but were instead based on a technique involving diffraction of X-rays. However, such methods have been found to be unreliable for this application, in particular owing to the spherical shape of the particles studied.

More recently, U.S. Pat. No. 5,956,147 proposed a method based on ellipsometry. A polarised light beam is transmitted elliptically onto a metallographic section of a particle. The reflected beam then passes into a quartz crystal, then into a polariser, before being directed to a photomultiplier tube, whose output signal is processed in order to extract from it a diattenuation coefficient which is correlated with the anisotropy. Such a method is also costly and complex to carry out.

The problem addressed by the invention is to overcome this problem by providing a method for measuring anisotropy which is reliable, rapid to carry out and requires a less expensive installation.

SUMMARY OF THE INVENTION

To that end, the invention relates to a measurement method of the above mentioned type, characterised in that it comprises the steps of:
transmitting the beam from the polarisation analyser to a device for acquiring digital images,
acquiring at least one digital image of the zone of the surface of the element and
processing the digital image acquired in order to measure the anisotropy.

According to specific embodiments, the method may comprise one or more of the following features, taken in isolation or in accordance with all technically possible combinations:
the method comprises the steps of:
acquiring a first image of the zone with a first analysis direction of the polarisation analyser,
acquiring a second image of the zone with a second analysis direction of the polarisation analyser and
dividing, pixel by pixel, the first image by the second image in order to form a cartographic image of measurements of the anisotropy of the zone;
the first analysis direction and the second analysis direction are substantially perpendicular;
the element having been at least partially produced by deposition of material in a deposition direction, the first direction is substantially perpendicular to the deposition direction adjacent to the zone;
the mean of the values of the pixels is calculated in at least one window of the cartographic image;
the window corresponds to a region of the surface which has a surface-area greater than 30 $\mu m^2$;
the method comprises the steps of:
rotating the analysis direction of the polarisation analyser through 360° about the propagation direction of the beam of light reflected, whilst at the same time acquiring digital images of the zone,
establishing, for each pixel, the maximum and minimum values obtained during the rotation of the analysis direction and forming a cartographic image of measurements of the anisotropy with, as a value for each pixel, the ratio of the maximum value relative to the minimum value established;

the beam transmitted is a beam of non-polarised light; and the element is a particle of nuclear fuel for a high temperature reactor.

The invention also relates to an installation for carrying out a method as defined above, characterised in that it comprises a light source for transmitting a beam of light onto the surface of the element comprising at least one fissile material, a polarisation analyser which has a modifiable analysis direction and which is intended to be passed through by the beam of light reflected by the surface, a device for acquiring digital images in order to receive the reflected beam of light after it has passed into the analyser and thereby acquiring at least one digital image of a zone of the surface of the element, and a unit for processing data in order to process the digital image acquired in order to measure the anisotropy.

According to specific embodiments, the device for acquiring digital images is a charge transfer camera.

BRIEF DESCRIPTION OF THE DRAWINGS

The invention will be better understood from a reading of the following description which is given purely by way of example and with reference to the appended drawings, in which.

DETAILED DESCRIPTION OF THE INVENTION

Figure 1:
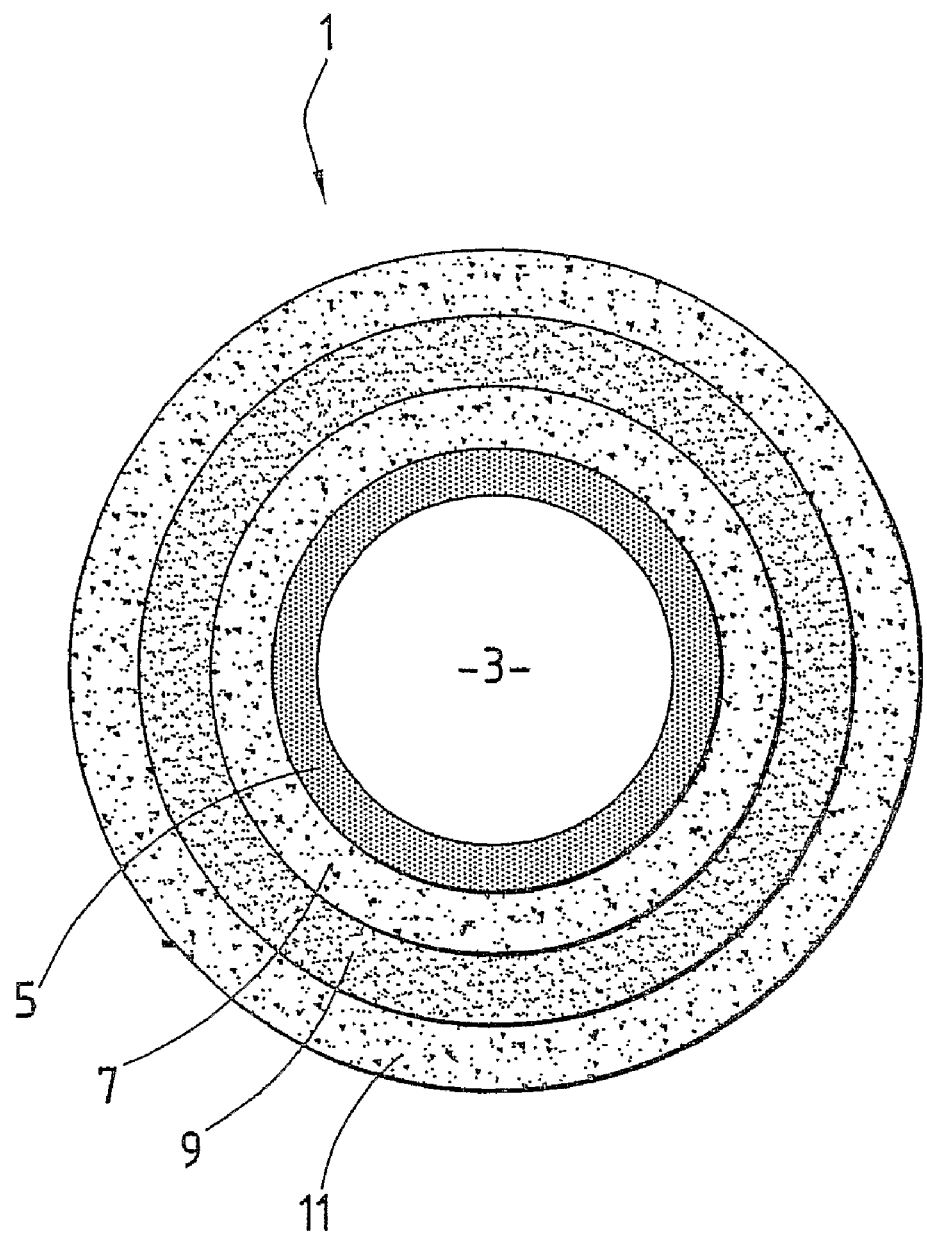
FIG. 1 is a schematic equatorial section illustrating the structure of a particle of nuclear fuel for a high temperature reactor.

FIG. 1 schematically illustrates a particle 1 of nuclear fuel for a high or very high temperature reactor (HTR/VHTR).

Conventionally, that particle 1 is generally of spherical shape and comprises successively, from the interior towards the exterior:

a core of fissile material 3, for example, based on $UO_2$ or UCO, a layer 5 of porous pyrocarbon, a first layer 7 of dense pyrocarbon, a layer 9 of silicon carbide and a second layer 11 of dense pyrocarbon.

When such a particle is used, the porous pyrocarbon acts as a reservoir for the fission gases, the silicon carbide acts as a barrier against the diffusion of the products of solid fission and the dense pyrocarbon brings about mechanical resistance to the pressure of the fission gases.

The core 3 has, for example, a diameter of approximately 500 μm and the layers 5, 7, 9 and 11 have respective thicknesses of, for example, 95, 40, 35 and 40 μm.

It will be appreciated that the relative dimensions of the core 3 and the layers 5, 7, 9 and 11 have not been complied with in FIG. 1.

The layers, in particular the pyrocarbon layers 5, 7, 11, are deposited, for example, by a chemical vapour deposition method carried out in a fluidised bed oven.

In order to be able to control the anisotropy of the layers surrounding the core 3, and in particular those of the layers 7 and 11 of dense pyrocarbon, an equatorial metallographic section of the particle 1 is prepared.

To that end, the particle 1 is embedded in a resin block 15 (FIG. 2) and the block 15 is polished as far as an equatorial plane. The surface 17 of the particle 1 which has been exposed in this manner may be observed.

Since the preparation of a metallographic section of this type is completely conventional, it will not be described in detail below.

Figure 2:
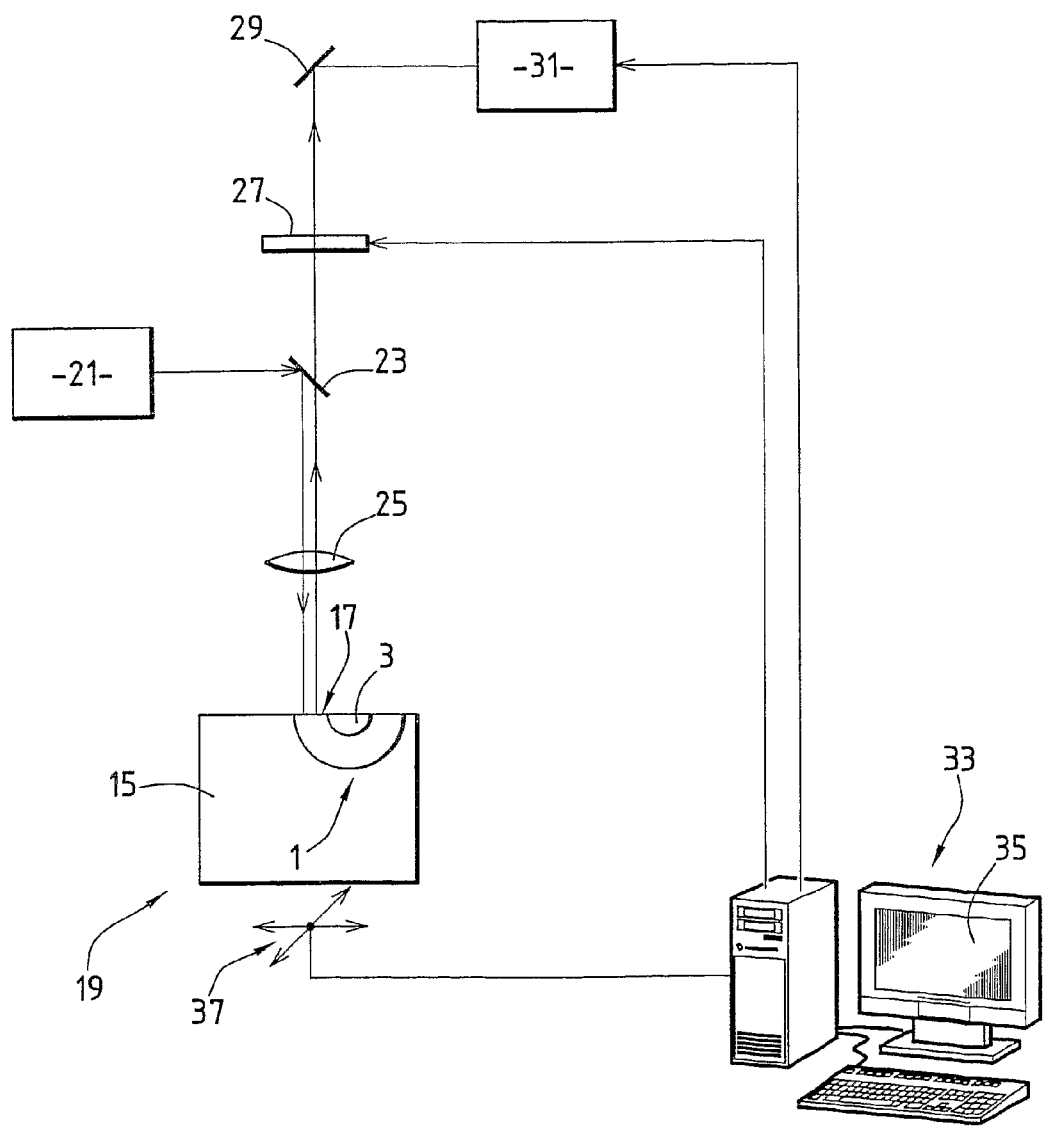
FIG. 2 is a schematic view illustrating an installation for carrying out a method for measuring the anisotropy according to the invention.

FIG. 2 shows the installation 19 which allows the anisotropy to be measured in the layers of the particle 1 which surround the core 3.

This installation 19 mainly comprises, in the example illustrated:

a light source 21, a semi-reflective plate 23, a lens 25 which forms an objective, a polarisation analyser 27, a reflective plate 29, a device 31 for acquiring digital images and a unit 33 for processing data.

The source 21 is, for example, a halogen lamp whose light beam produced may optionally be transmitted via an optical fibre. The light beam from the source 21 is directed by the semi-reflective plate 23 through the lens 25, towards the surface 17 to be observed.

The presence of anisotropy at the surface 17 tends to polarise the light reflected by the surface 17.

The beam reflected by the surface 17 passes through the lens 25, then the semi-reflective plate 23 and the analyser 27.

In conventional manner, the analyser 27 preferentially allows the polarised light to pass in an analysis direction. That selected analysis direction may be modified, for example, by rotating a portion of the analyser 27. During such a modification, the analysis direction rotates about the propagation direction of the beam reflected by the surface 17.

The light beam from the analyser 27 is directed by the reflective plate 29 towards the device 31 for acquiring digital images.

That device 31 is, for example, a digital camera of the charge transfer type, or charge coupled device (CCD). It is possible, for example, to use a Nikon (registered mark) camera of the DXM 1200 type.

Therefore, the camera 31 can acquire digital images of the surface 17 owing to the beam reflected by the surface 17 and directed towards the camera 31.

The digital data acquired by the camera 31 are supplied to the unit 33 for processing data.

The unit 33 comprises, for example, a micro-processor provided, inter alia, with display means in the form of a screen 35. The unit 33 is also connected to means 37 which allow the block 15 to be supported and displaced perpendicularly relative to the beam incident to the surface 17, for example, in two directions orthogonal to each other. Such a displacement may be carried out before the analysis in order to correctly position the surface 17.

The means 37 may also allow the block 15 to be moved parallel with the incident beam. The unit 33 can then automatically bring about the focusing by controlling the height of the block 15. Advantageously, the unit 33 comprises shape recognition software which allows that focusing to be carried out.

The unit 33 can also bring about the control of the analyser 27 in order to modify its analysis direction.

Figure 3:
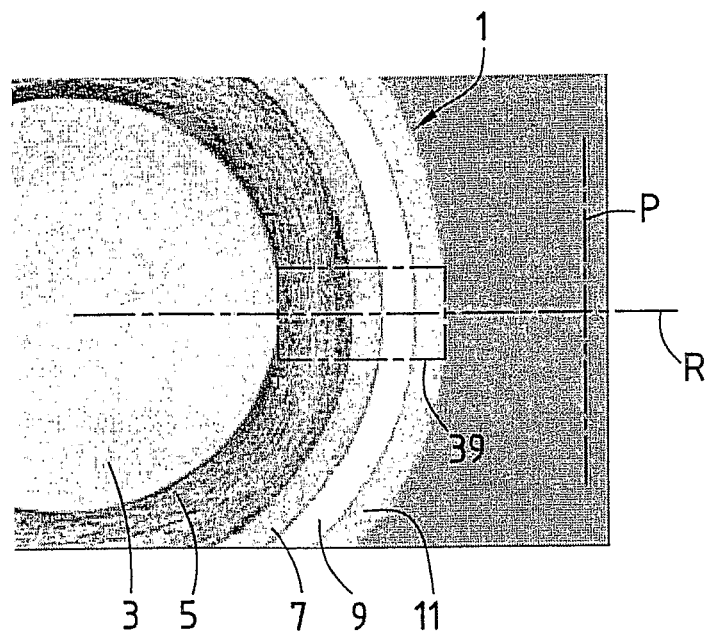
FIGS. 3 and 4 are the images acquired when a method according to the invention is carried out.

FIG. 3 illustrates a digital image of the surface 17 acquired by the camera 31. That image covers in particular a zone 39 of the surface 17 which extends in a radial direction R of the particle 1 of the core 3 as far as the layer 11. The radial direction R substantially corresponds to the deposition direction when the pyrocarbon layers 7 and 11 are produced.

In a first embodiment of the method for measuring the anisotropy, a first image of the surface 17 of the particle 1 is acquired with, as the analysis direction of the analyser 27, a direction substantially orthogonal to the direction R. The analysis direction P is indicated in FIG. 3 which shows the first image acquired.

Figure 4:
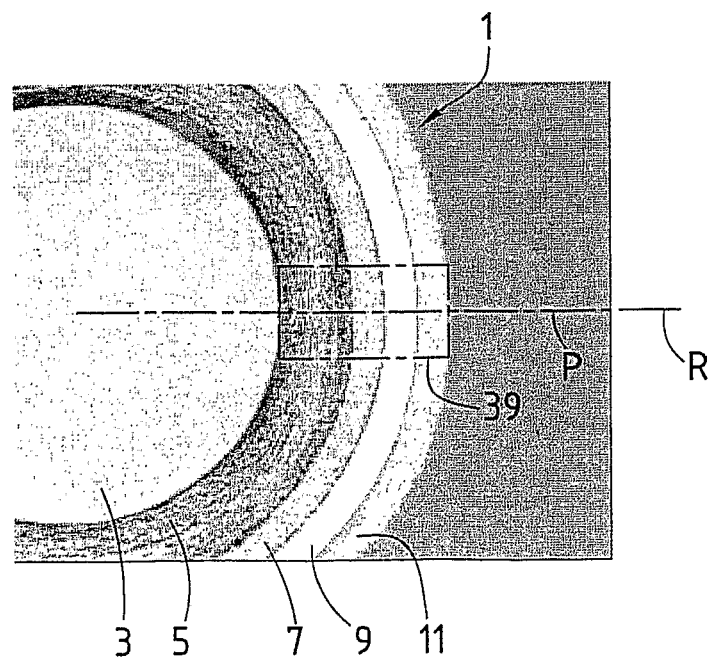

The selected analysis direction P of the analyser 27 is then modified so that the direction P is substantially parallel with the deposition direction R. A second digital image of the surface 17 is then acquired (FIG. 4).

In order to measure the anisotropy in the particle 1, and in particular in the zone 39 of the surface 17, the two images acquired will be digitally processed.

Figure 5:
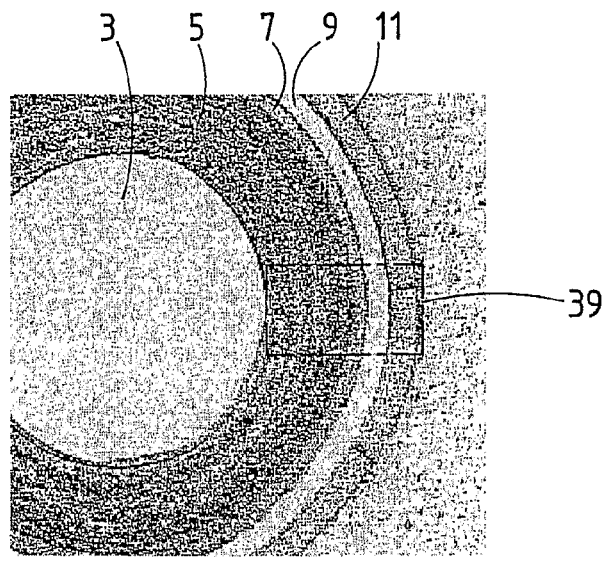
FIG. 5 is an image resulting from the digital processing when a method according to the invention is carried out.

To that end, the first image will be divided, pixel by pixel, by the second image. Thus, the image of FIG. 5 is obtained.

The value of each pixel of the image obtained in this manner therefore corresponds to the relationship:

of the intensity $i_\parallel$ of the beam reflected by the corresponding point of the surface 17 after analysis parallel with the surface of deposition, that is to say, the value of the corresponding pixel of the first image (FIG. 3), and the intensity $i_\perp$ of the beam reflected by the corresponding point of the surface 17, then analysed perpendicularly to the surface of deposition, that is to say, the value of the corresponding pixel of the second image (FIG. 4).

That relationship between intensities is qualified by a degree of anisotropy of reflectance or DAR:

$$DAR = \frac{i_\parallel}{i_\perp}$$

The image obtained can be displayed in false colours, that is to say, with colours ranging from blue to red in accordance with the DAR value obtained for each pixel.

Figure 6:
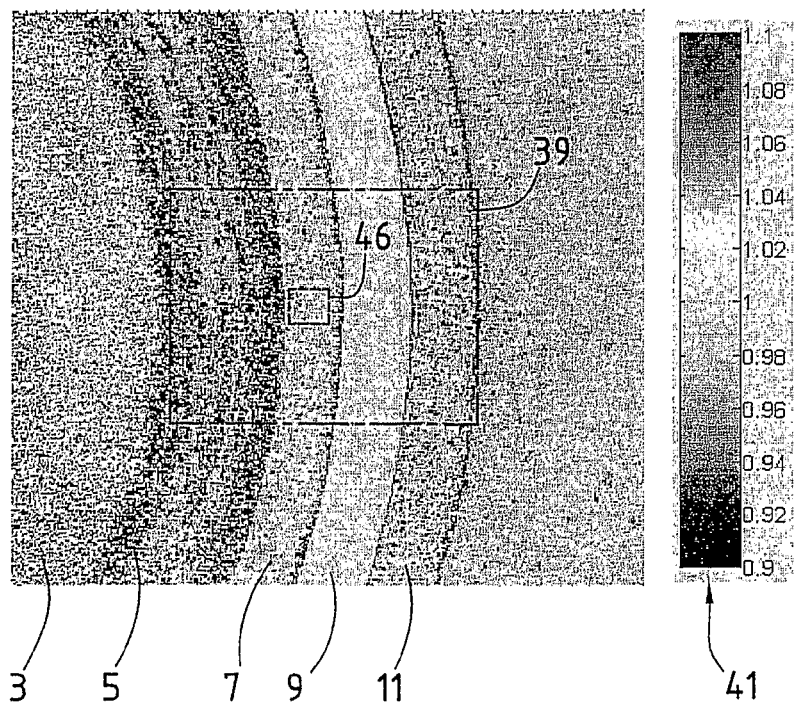
FIG. 6 is an enlarged view of part of the image of FIG. 5.

FIG. 6 shows a display of this type, enlarged in the zone 39. The reference numeral 41 denotes the scale used. The blue corresponds to DAR values in the order of 0.9, the green to DAR values in the order of 1 and the red to DAR values in the order of 1.1.

A DAR value of approximately 1 characterises good isotropy whilst values greater than 1 characterise anisotropy. Anisotropy is intended to refer to a deviation with respect to isotropy. DAR values less than 1 correspond, for example, to the presence of occurrences of porosity bringing about artefacts of measurements.

Therefore, a bi-dimensional mapping of the measurements of the anisotropy of the zone 39 is thereby obtained.

Figure 7:
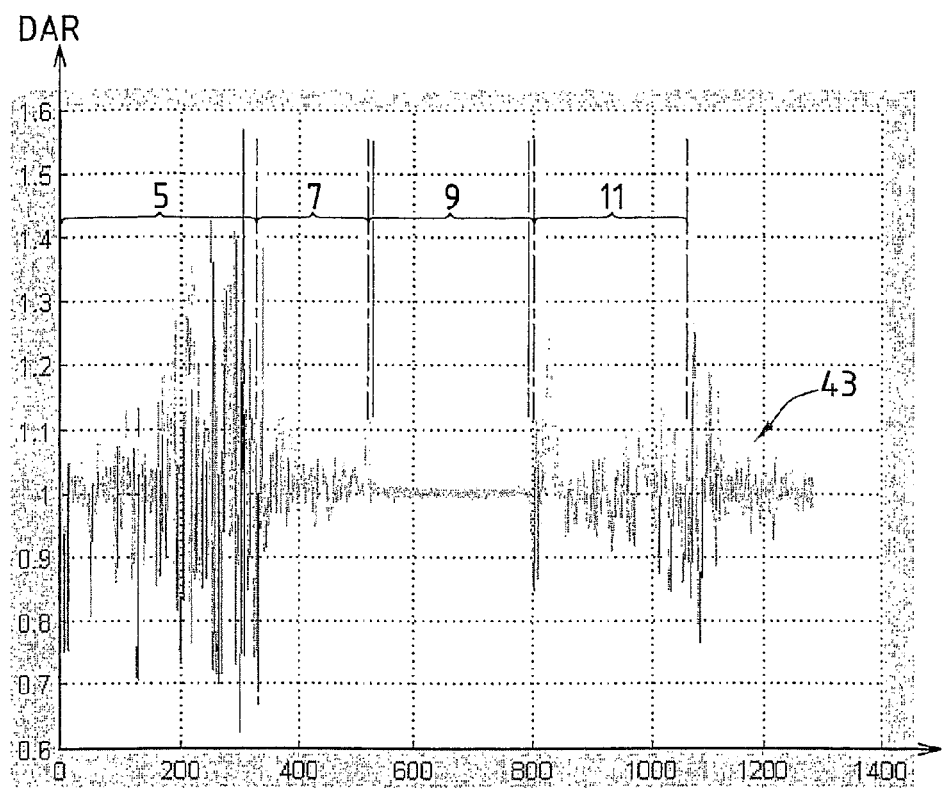
FIG. 7 is a line showing the radial profile of the anisotropy measured by means of a method according to the invention and FIGS. 8 and 9 are lines allowing the reliability of the measurements carried out to be improved.

The profile of the DAR can readily be deduced therefrom in the radial direction R, as illustrated in FIG. 7. In that Figure, the reference numeral 43 denotes the line representing that profile. The abscissae correspond to the radial position, the origin being at the start of the layer 5 at the boundary with the core 3. The ordinates correspond to the DAR values. It is possible to distinguish, on the line 43, the various portions corresponding to the layers 5, 7, 9 and 11.

As can be seen in FIG. 7, the portion of the line 43 corresponding to the layer 9 is practically rectilinear and is substantially equal to 1. This is because the corresponding-layer of silicon carbide is dense and very isotropic. The DAR value is therefore affected by noise only very slightly.

However, it is apparent that the DAR measurements carried out in this manner are greatly affected by noise at the layers of dense pyrocarbon 7 and 11 and that, therefore, the measurement at the scale of the pixel is not completely reliable.

Figure 8:
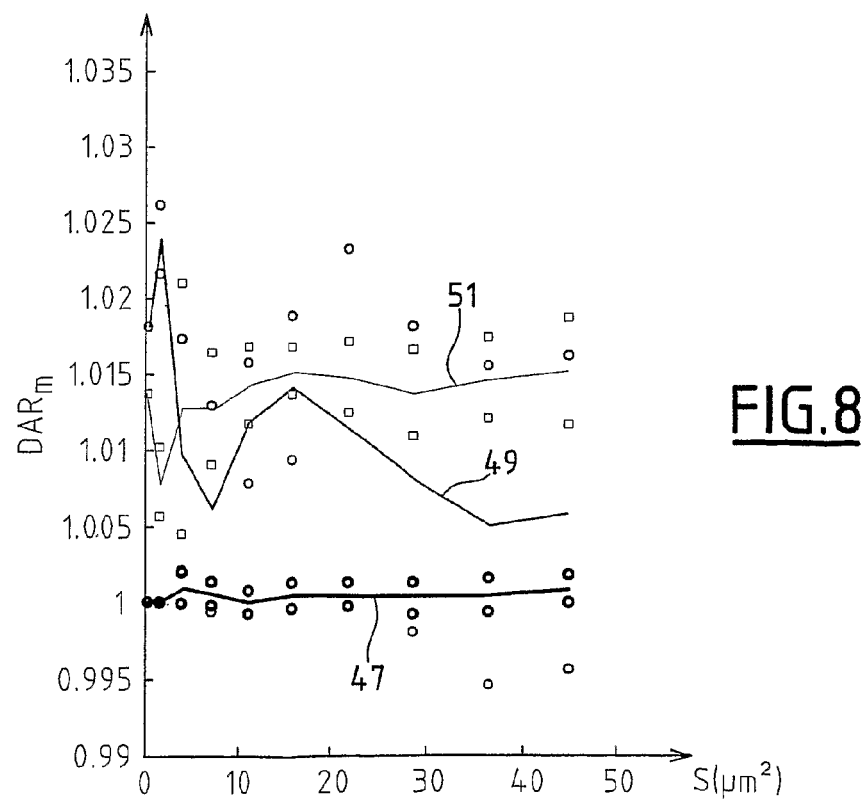

In order to overcome that disadvantage, it is possible to carry out, for example, for each layer of dense pyrocarbon 7 and 11, a calculation of the mean $DAR_m$ of the DAR values in a calculation window which is, for example, of a square shape. Such a window is indicated in FIG. 6. FIG. 8 illustrates the development of the $DAR_m$ values in accordance with the surface-area S in square micrometers of the region of the surface 17 corresponding to the calculation window.

The line 47 corresponds to a calculation on a window located in the layer of silicon carbide 9. The bold circles located at one side and the other indicate the standard deviation.

The lines 49 and 51 correspond to the layers of dense pyrocarbon 7 and 11, respectively, and the squares and the circles correspond to the corresponding standard deviations.

Figure 9:
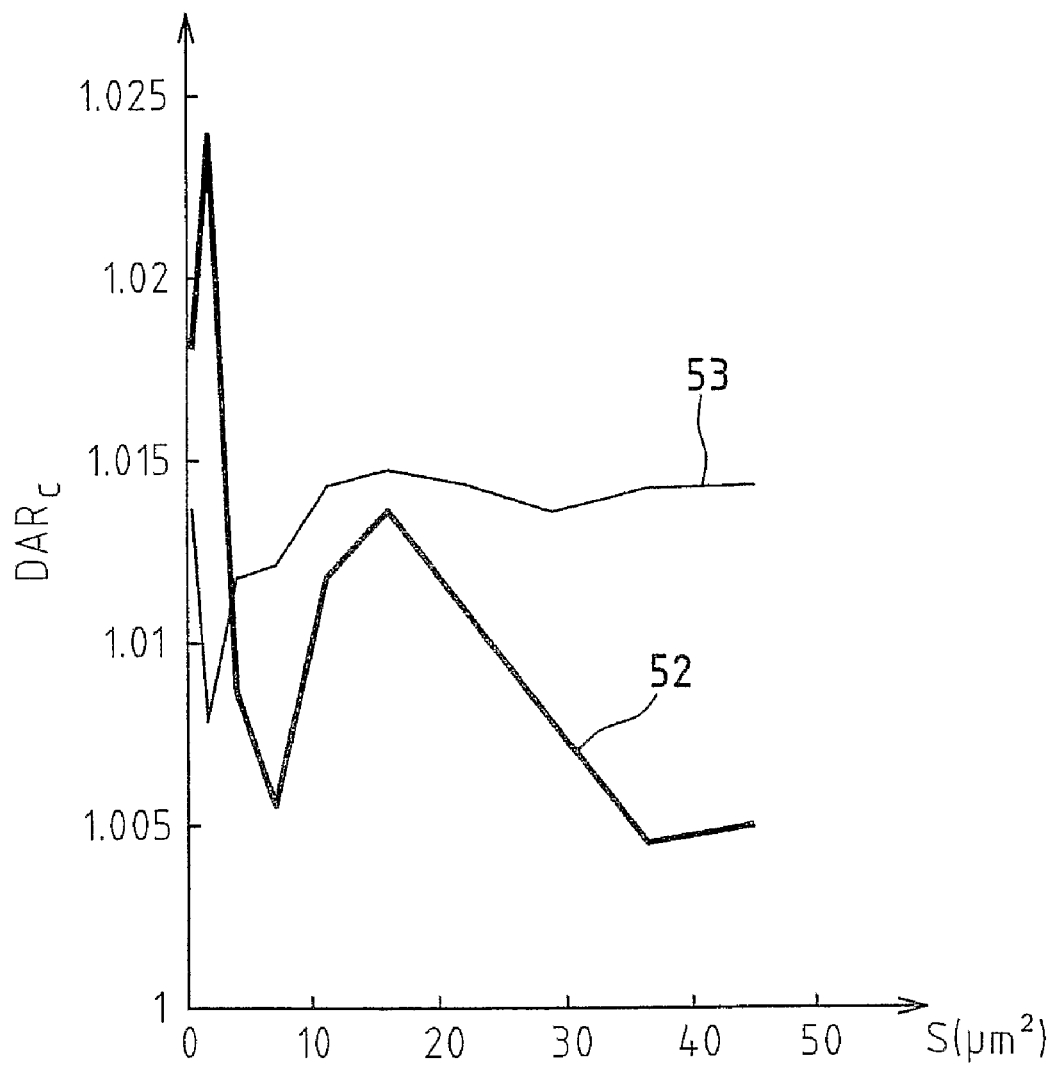

It is possible, for example, to calibrate the $DAR_m$ values calculated relative to the $DAR_m$ values calculated for the layer of silicon carbide 9. Thus, FIG. 9 illustrates the two lines obtained 52 and 53 for the layers of dense pyrocarbon 7 and 11, respectively.

The ordinates correspond to the corrected DAR value $DAR_c$ calculated in this manner:

$$DAR_c = \frac{DAR_m}{DAR_{m(SiC)}}$$

As will be appreciated, the $DAR_c$ values appear to be stable for surface-areas S of approximately 30 μm².

Therefore, calculation windows will preferably be used corresponding to surface-areas greater than 30 μm² and, in a still further preferred manner, greater than 40 μm².

Since the particle 1 is spherical, it is possible, assuming that the symmetry of revolution is complied with, to consider that the measurements carried out in the zone 39 characterise the whole of the particle 1.

It is also possible, if the first and second images mentioned above are views of the whole of the particle 1, to carry out, for example, calculations of the DAR values, and optionally $DAR_m$ and $DAR_c$, at four points located, for example, at the north, east, south and west poles of a particle, as viewed in a meridian section.

The values of the pixels of the first image are then divided, in the east and west zones, by the values of pixels of the second image and, for the north and south zones, the values of the pixels of the second image are divided by the values of pixels of the first image.

In this manner, it is possible to obtain measurements of the anisotropy in four zones located at 90° relative to each other with respect to the centre of the particle 1.

A method has been carried out for measuring the anisotropy as described above on particles 1 which had been further characterised by a method in accordance with the prior art.

The method according to the invention allows measurements of the anisotropy to be obtained which are reliable with reduced standard deviations.

It will further be appreciated that the above-described method requires, in order to be carried out, an installation 19 of reduced cost, in particular because it does not use a photometer.

Furthermore, the method is very rapid to carry out because it is possible, based on the two images acquired (FIGS. 3 and 4), to measure the anisotropy simultaneously in the layers 7 and 11, and optionally in other layers.

By way of a variant, the installation 19 can, in addition to or in place of the digital processing described above, carry out other operations for digitally processing one or more images acquired in order to measure the anisotropy of the surface 17.

By way of example, it is possible to rotate the analysis direction P of the analyser 27 through 360° whilst at the same time acquiring the corresponding images of the surface 17. Subsequently, an image is formed whose value for each pixel corresponds to the ratio of the maximum value or intensity $I_{max}$ relative to the minimum intensity or value $I_{min}$ obtained for the same pixel during the rotation of the analysis direction P. Thus, an image is obtained which is a mapping of a parameter measuring the anisotropy which is referred to as RAPAX:

$$RAPAX = \frac{I_{max}}{I_{min}}$$

That parameter has the advantage of being free from the inaccuracy linked to the angular position of the analysis direction P of the analyser 27.

As before, it is possible to calculate a mean RAPAX, $RAPAX_m$, by averaging out the intensities measured over calculation windows. That value can itself be calibrated relative to the $RAPAX_m$ calculated for the layer of silicon carbide 9:

$$RAPAX_c = \frac{RAPAX_m}{RAPAX_{mSiC}}$$

It will also be appreciated that the device for acquiring digital images 31 can be positioned in alignment with the surface 17 so that the reflective plate 29 is dispensed with.

The above-described method can be used for measuring the anisotropy in elements other than particles of nuclear fuel for an HTR/VHTR type reactor. These will generally be elements comprising at least one fissile material.

The invention claimed is:

1. A method for measuring anisotropy of a zone of a surface of an element comprising at least one fissile material, the method comprising:
    transmitting a beam of light onto the surface; and
    passing the beam of light reflected by the surface into a polarisation analyser having a modifiable analysis direction, wherein the method further comprises:
        transmitting the beam from the polarisation analyser to a device for acquiring digital images,
        acquiring a first digital image of the zone of the surface of the element with a first analysis direction of the polarisation analyser,
        acquiring a second digital image of the zone of the surface of the element with a second analysis direction of the polarisation analyzer, and
        processing the first digital image and the second digital image acquired in order to measure the anisotropy by dividing, pixel by pixel, the first digital image by the second digital image in order to form a cartographic image of measurements of the anisotropy of the zone.

2. The method according to claim 1, wherein the beam transmitted is a beam of non-polarised light.

3. The method according to claim 1, wherein the element is a particle of nuclear fuel for a high temperature reactor.

4. The method according to claim 1, wherein the first analysis direction and the second analysis direction are substantially perpendicular.

5. The method according to claim 1, wherein the mean of the values of the pixels is calculated in at least one window of the cartographic image.

6. The method according to claim 4, wherein the element having been at least partially produced by deposition of material in a deposition direction, the first analysis direction is substantially perpendicular to the deposition direction adjacent to the zone.

7. The method according to claim 5, wherein the window corresponds to a region of the surface which has a surface-area greater than 30 μm2.

8. An installation which comprises:
    a light source configured to transmit a beam of light onto a surface of an element comprising at least one fissile material,
    a polarisation analyser having a modifiable analysis direction and configured to be passed through by the beam of light reflected by the surface,
    a device configured to acquire digital images and to receive the reflected beam of light after said reflected beam of light has passed into the polarisation analyser, and thereby configured to acquire a first digital image of a zone of the surface of the element with a first analysis direction of the polarisation analyser and to acquire a second digital image of the zone of the surface of the element with a second analysis direction of the polarisation analyser, and
    a unit configured to process the first digital image and the second digital image acquired and to measure the anisotropy by dividing, pixel by pixel, the first digital image by the second digital image to form a cartographic image of measurements of the anisotropy of the zone.

9. An Installation according to claim 8, wherein the device configured to acquire digital images is a charge transfer camera.

10. A method for measuring anisotropy of a zone of a surface of an element comprising at least one fissile material, the method comprising:
    transmitting a beam of light onto the surface; and
    passing the beam of light reflected by the surface into a polarisation analyser having a modifiable analysis direction, wherein the method further comprises:
        transmitting the beam from the polarisation analyser to a device for acquiring digital images,
        rotating the analysis direction of the polarisation analyser through 360° about a propagation direction of the beam of light reflected, while at the same time acquiring digital images of the zone of the surface of the element, and
        processing the digital images acquired in order to measure the anisotropy, by:
            establishing, for each pixel, the maximum and minimum values obtained during the rotation of the analysis direction, and forming a cartographic image of measurements of the anisotropy with, as a value for each pixel, a ratio of the maximum value relative to the minimum value established.

11. The method according to claim 10, wherein the beam transmitted is a beam of non-polarised light.

12. The method according to claim 10, wherein the element is a particle of nuclear fuel for a high temperature reactor.

13. An installation which comprises:
- a light source configured to transmit a beam of light onto a surface of an element comprising at least one fissile material,
- a polarisation analyser having a modifiable analysis direction and configured to be passed through by the beam of light reflected by the surface,
- a device configured to acquire digital images and to receive the reflected beam of light after said reflected beam of light has passed into the polarisation analyser, and thereby configured to acquire digital images of a zone of the surface of the element while at the same time the analysis direction of the polarisation analyser is rotated through 360° about a propagation direction of the beam of light reflected, and
- a unit configured to process the digital images acquired and to measure anisotropy by:
    - establishing, for each pixel, maximum and minimum values obtained during the rotation of the analysis direction, and
    - forming a cartographic image of measurements of the anisotropy with, as a value for each pixel, a ratio of the maximum value relative to the minimum value established.

14. The Installation according to claim 13, wherein the device configured to acquire digital images is a charge transfer camera.

* * * * *